(12) United States Patent
Fang et al.

(10) Patent No.: US 7,542,132 B2
(45) Date of Patent: Jun. 2, 2009

(54) RAMAN SPECTROSCOPY AS INTEGRATED CHEMICAL METROLOGY

(75) Inventors: Hongbin Fang, San Jose, CA (US); Josh Golden, Santa Cruz, CA (US); Timothy W. Weidman, Sunnyvale, CA (US); Yaxin Wang, Fremont, CA (US); Arulkumar Shanmugasundram, Sunnyvale, CA (US)

(73) Assignee: Applied Materials, Inc., Santa Clara, CA (US)

( * ) Notice: Subject to any disclaimer, the term of this patent is extended or adjusted under 35 U.S.C. 154(b) by 0 days.

(21) Appl. No.: 11/830,202

(22) Filed: Jul. 30, 2007

(65) Prior Publication Data

US 2008/0024762 A1    Jan. 31, 2008

Related U.S. Application Data

(60) Provisional application No. 60/820,840, filed on Jul. 31, 2006.

(51) Int. Cl.
*G01J 3/44* (2006.01)
*G01N 21/65* (2006.01)

(52) U.S. Cl. .......................... 356/72; 356/301

(58) Field of Classification Search ............... 356/301
See application file for complete search history.

(56) References Cited

U.S. PATENT DOCUMENTS

| 2003/0049858 A1 | 3/2003 | Golden et al. |
| 2004/0046121 A1 | 3/2004 | Golden et al. |
| 2005/0181226 A1 | 8/2005 | Weidman et al. |

FOREIGN PATENT DOCUMENTS

| JP | 56-55842 | * | 5/1981 |
| WO | WO 03/008919 | | 1/2003 |

\* cited by examiner

*Primary Examiner*—F. L Evans
(74) *Attorney, Agent, or Firm*—Patterson & Sheridan

(57) ABSTRACT

A method for measuring the concentration of the metal solution and reducing agent solution within the electroless plating solution is disclosed. Raman spectroscopy is used to measure the concentration of each solution within the electroless plating solution after they have been mixed together. By measuring the concentration of each solution prior to providing the solution to a plating cell, the concentration of the individual solutions can be adjusted so that the targeted concentration of each solution is achieved. Additionally, each solution can be individually analyzed using Raman spectroscopy prior to mixing with the other solutions. Based upon the Raman spectroscopy measurements of the individual solutions prior to mixing, the individual components that make up each solution can be adjusted prior to mixing so that the targeted component concentration can be achieved.

18 Claims, 6 Drawing Sheets

RAMAN SPECTROSCOPY AS INTEGRATED CHEMICAL METROLOGY

CROSS-REFERENCE TO RELATED APPLICATIONS

This application claims benefit of U.S. provisional patent application Ser. No. 60/820,840 (APPM/10974L), filed Jul. 31, 2006, which is herein incorporated by reference.

BACKGROUND OF THE INVENTION

1. Field of the Invention

Embodiments of the present invention generally relate to a method and an apparatus for measuring an electroless plating solution and individual components of the electroless plating solution using Raman spectroscopy.

2. Description of the Related Art

Recent improvements in circuitry of ultra-large scale integration (ULSI) on substrates indicate that future generations of integrated circuit (IC) semiconductor devices will require smaller multi-level metallization. The multilevel interconnects that lie at the heart of this technology require planarization of interconnects formed in high aspect ratio features, including contacts, vias, lines and other features. Reliable formation of these interconnects is very important to the success of ULSI and to the continued effort to increase circuit density by decreasing the dimensions of semiconductor features and decreasing the widths of interconnects (e.g., lines) to 0.13 μm and less. Currently, copper and its alloys have become the metals of choice for sub-micron interconnect technology because copper (Cu) has a lower resistivity than aluminum (Al) (i.e., 1.67 $\mu\Omega$-cm for Cu as compared to 3.1 $\mu\Omega$-cm for Al), a higher current carrying capacity, and significantly higher electromigration resistance.

One method for copper deposition is metal plating. Metal plating is used in a large variety of industrial processes. Plating systems, in which an object is placed in a plating solution to apply a metallic coating to the object, are well known in the art. Metal plating is used to plate a variety of metals, such as for example, copper, zinc, nickel, and gold. Many metals are plated simply by immersion in a metal plating bath that uses a chemical reducing agent, called electroless plating.

The electroless plating solution comprises a metal solution and a reducing agent solution. The solutions are mixed together to form the electroless plating solution that is provided to the substrate that is to be plated. It is important that the individual solutions be mixed together in the proper concentration so that electroless deposition can proceed in the most efficient manner possible. Additionally, each individual solution of the electroless plating solution is comprised of a plurality of components. It is important that each individual solution have the proper concentration of individual components so that the solutions can be properly used to plate the substrate.

Therefore, there is a need in the art for a method and apparatus capable of measuring the combined concentration of components in an electroless plating solution. There is also a need in the art for a method and apparatus capable of measuring the concentration of the individual components that comprise each solution that is mixed to form the electroless plating solution.

SUMMARY OF THE INVENTION

The present invention generally comprises a method of electroless plating using in-situ Raman spectroscopy to measure the solution concentrations within the electroless plating solution and the individual components of the solutions that make up the electroless plating solution. Raman spectroscopy is used to measure the concentration of each solution within the electroless plating solution after they have been mixed together. By measuring the concentration of each solution prior to providing the solution to a plating cell, the concentration of the individual solutions can be adjusted so that the targeted concentration of each solution is achieved. Additionally, each solution can be individually analyzed using Raman spectroscopy prior to mixing with the other solutions. Based upon the Raman spectroscopy measurements of the individual solutions prior to mixing, the individual components that make up each solution can be adjusted prior to mixing so that the targeted component concentration can be achieved.

In one embodiment, an electroless deposition method is disclosed. The method comprises mixing a metal solution and a reducing agent solution together to form an electroless plating solution, measuring the concentration of the metal solution and the reducing agent solution in the electroless solution using Raman spectroscopy, and plating a substrate using the electroless solution.

In another embodiment, an electroless deposition method is also disclosed. The method comprises mixing a plurality of components together to form a metal solution, measuring the concentration of the components of the metal solution using Raman spectroscopy, mixing a plurality of components together to form a reducing agent solution, measuring the concentration of the components of the reducing agent solution using Raman spectroscopy, mixing the metal solution and the reducing agent solution together to form a electroless solution, and plating a substrate using the electroless solution.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

To facilitate understanding, identical reference numerals have been used, where possible, to designate identical elements that are common to the figures. It is contemplated that elements disclosed in one embodiment may be beneficially utilized on other embodiments without specific recitation.

DETAILED DESCRIPTION

Figure 1:
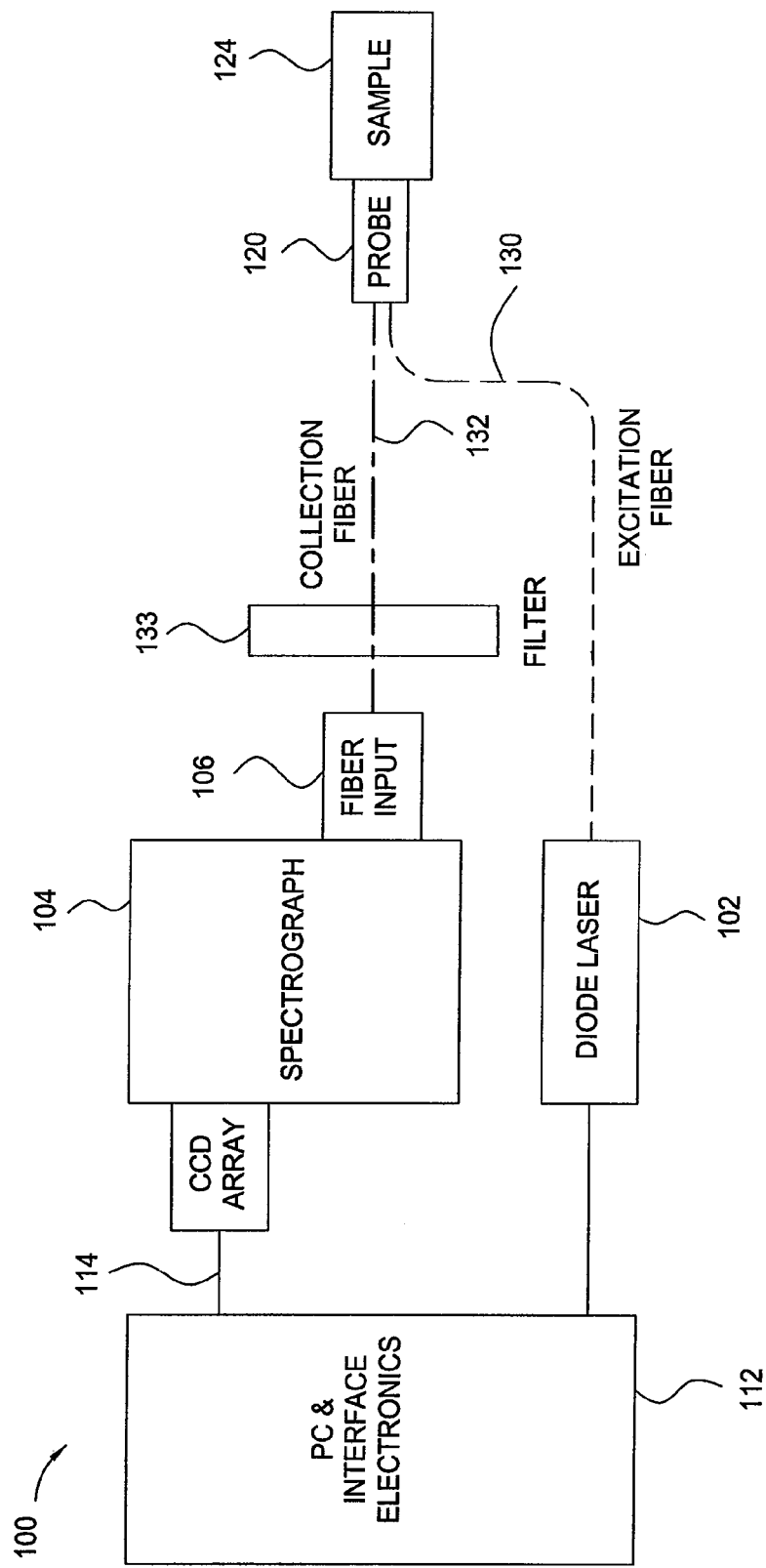
FIG. 1 is a schematic diagram illustrating the Raman device of one embodiment of the present invention.

The present invention comprises in-situ Raman spectroscopy measuring of an electroless plating solution and the components of the individual solutions that make up the electroless plating solution. The electroless plating process is sensitive to concentration variations of each component of the electroless plating solution. Some of the components in the electroless plating solution will degrade to form byproducts. The byproducts will negatively impact the film deposition process. It is beneficial to control the chemistry of the electroless plating solution at all stages so that the concentration of the components that make up the electroplating solution can be controlled. Raman spectroscopy is an attractive method for analyzing the components in an electroless plating solution. Raman spectroscopy is non-invasive (i.e., it does not contact the chemicals), uses no reagent (i.e., it drives down the cost and minimizes the waste stream so that it is more environmentally friendly), has a high accuracy for most of the components in the electroless plating solution chemistry, and is fast compared to other measurement techniques.

Every poly-atomic molecule has its own distinct vibrational Raman bands in the infrared wavelength. Raman spectroscopy is used in the research community and the chemical and pharmaceutical industries for chemical identification and process control. With more and more semiconductor processes using wet chemistries (i.e., chemical mechanical polishing (CMP), electrochemical mechanical polishing (ECMP), electropolishing, wet cleaning, electrochemical plating (ECP), and electroless (ELESS)), Raman spectroscopy can be used for better process control.

Raman spectroscopy may be used to measure the concentration of components in polishing compositions used for electropolishing, CMP, and ECMP. It may also be used to measure the concentration of plating baths such as ECP and ELESS. Additionally, it may be used to measure the concentration of solutions used for wet cleaning.

The Raman signal is proportional to the molecular concentration in the solution. Concentration variations of less than 5 percent can be easily detected by Raman spectroscopy. Raman spectroscopy is advantageous for aqueous solutions. If infrared absorbance spectroscopy were used, water, which has a very strong absorption in infrared wavelength, would obscure the spectrum of the other components in the solution. With the advancement of Raman related techniques, such as surface enhanced Raman spectroscopy, more and more applications in the semiconductor manufacturing processes are possible. In surface enhanced Raman spectroscopy, the presence of some specific particles, such as nanoparticles, can greatly improve the detection limit (i.e., the sensitivity) of the Raman spectroscopy.

In electroless deposition, a plating bath is prepared for each wafer that is processed. Raman spectroscopy can be used to analyze the chemical parts of the electroless plating solution separately to ensure that no degradation has occurred. Once the individual solutions are mixed together, the mixing ratio can also be verified. Therefore, Raman spectroscopy can be used not only for chemical quality control, but also for hardware reliability control.

For hardware reliability control, a user defined concentration is measured to test the hardware reliability. For example, a user will chose a specific concentration of a component. In order to achieve the user defined concentration, the flow rates of the various components are set so that the user defined concentration is achieved. The hardware reliability is tested by measuring the concentration. As the concentration is measured over time, it should remain constant without any adjustment of the flow rates. However, if the concentration does change, then the hardware has reliability issues that need to be addressed. Therefore, Raman spectroscopy may be used to verify hardware reliability.

A Raman spectroscopy sensor 100, particularly suitable for detection of solution components in the metal solution and the reducing agent solution, in accordance with one embodiment of the present invention is illustrated in FIG. 1. The sensor 100 generally includes a monochromatic light source 102, a spectrograph 104, a probe 120 that is coupled to the light source 102 and the spectrograph 104 through an excitation fiber 130 and a collection fiber 132 respectively, for delivering incident light to and collecting scattered light from a sample location 124, a fiber input and a personal computer date processor with interface output from the spectrograph 104.

The sample location 124 may be a separate container in which a sample of the solution is contained for concentration measurement. Alternatively, the sample location may be a substantially clear window within the system through which the solution flows. The window should be sufficiently clear to ensure that the window does not interfere with metrology or Raman spectroscopy. In one embodiment, the sample location is a quartz tube within the system through which the solution flows during processing. Raman spectroscopy may be used to measure the concentration of the solution through the quartz window without wasting valuable solution as a sample. Additionally, by measuring the concentration through a window, the Raman spectroscopy provides an accurate, non-invasive measurement of the solution.

In the embodiment shown in FIG. 1, the monochromatic light source 102 is preferably comprised of a frequency doubled YAG diode laser. The diode laser is powered by a power supply (not shown). In one embodiment, the excitation light from the diode laser is focused onto a fiber end of the excitation fiber 130 which conducts the incident light to the probe 120 for focusing into a sample location 124.

A plating solution to be analyzed enters the sample location 124 either through normal operating circulation of the bulk bath or via one or more pumps (not shown). The bath interacts with the excitation light delivered by the excitation fiber 130 to the probe 120 to yield Raman scattered light. Light scattered from the solution, (i.e., the Raman radiation or signal), is collected by the probe 120 and delivered to the fiber input 106 via the collection fiber 132. From the fiber input 106, collected scattered light passes into the spectrograph 104 wherein it is analyzed to yield a spectrum which is quantified in real time via a charge-coupled device (CCD) array 110. A CCD is a light sensitive integrated circuit that quantifies the intensity of the light by converting the light into an electrical charge.

The Raman signal preferably passes through a filter 133 which is preferably a reject filter chosen to filter out light at the incident wavelength to prevent swamping of the CCD detector, and is coupled to fiber optic borosilicate glass, prior to analysis in the spectrograph. Borosilicate glass fiber has a Raman shift of a well defined wavelength notch for baseline frequency calibration. Various spectrographs 104 may be used. Exemplary Raman spectrographs can be purchased from Kaiser Optical Systems, Inc. and Horiba Jobin Yvon. A serial interface 114 may be provided for coupling the processed signal to a computer system 112 for display and/or analysis.

The spectrometer is optical and mechanical in nature. The Raman scattered light delivered via the collection fiber 132 from the sample 124 is projected onto the CCD array 110. The CCD data spectrum is then analyzed to calculate the concentration levels of additives and byproducts. The computer system 112 preferably consists of a computer, a CCD controller card that plugs into the computer mother board, communication RC cards such as a modem and an Ethernet card among others, and digital and analog input/output ports.

Figure 2:
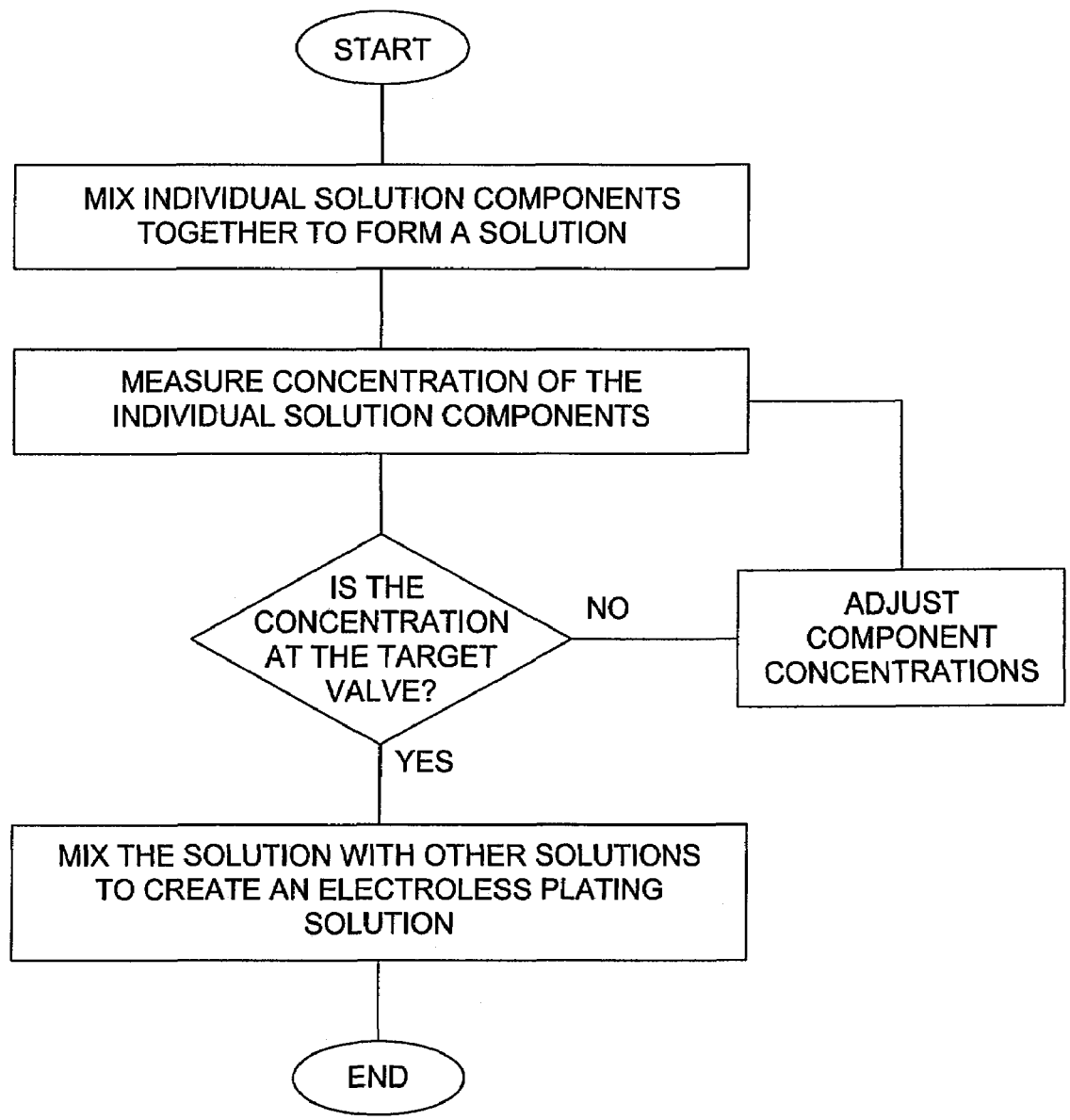
FIG. 2 is a flow chart for measuring the concentration of the individual components of the individual solutions that make up the electroless plating solution.

FIG. 2 is a flow chart showing one embodiment of the process involved in using Raman spectroscopy to measure the concentration of each component that is within each solution that comprise the electroless plating solution. The components of a particular solution are combined within a single stream of solution. After the components are mixed together, the concentration of the individual components within the solution is measured using Raman spectroscopy. If the concentration is at the target valve for each component, then no change needs to be made to the solution. If, however, the concentration of any one component is not at the target valve, then the concentration needs to be adjusted so that the target valve for each component is met. For example, the concentration of a component of the buffered cleaning solution can be measured in relation to the entire buffered cleaning solution. Similarly, the concentration of a component of the metal solution can be measured in relation to the entire metal solution. Finally, the concentration of a component of the reducing agent solution can be measured in relation to the entire reducing agent solution.

When the Raman spectroscopic measurements reveal that the concentration of the solution is not at the target valve, the solution may either be adjusted by adjusting the flow rates of the components or the solution may be discarded. In one embodiment, the solution is discarded and the flow rates are adjusted. Additional measurements occur to ensure that the desired concentration is achieved. Once the solution achieves the desired concentration, the solution will no longer need to be discarded. Once the desired concentration is achieved, the solution may be used. In one embodiment, the solution is not discarded, but rather, is recycled through the system.

Figure 3:
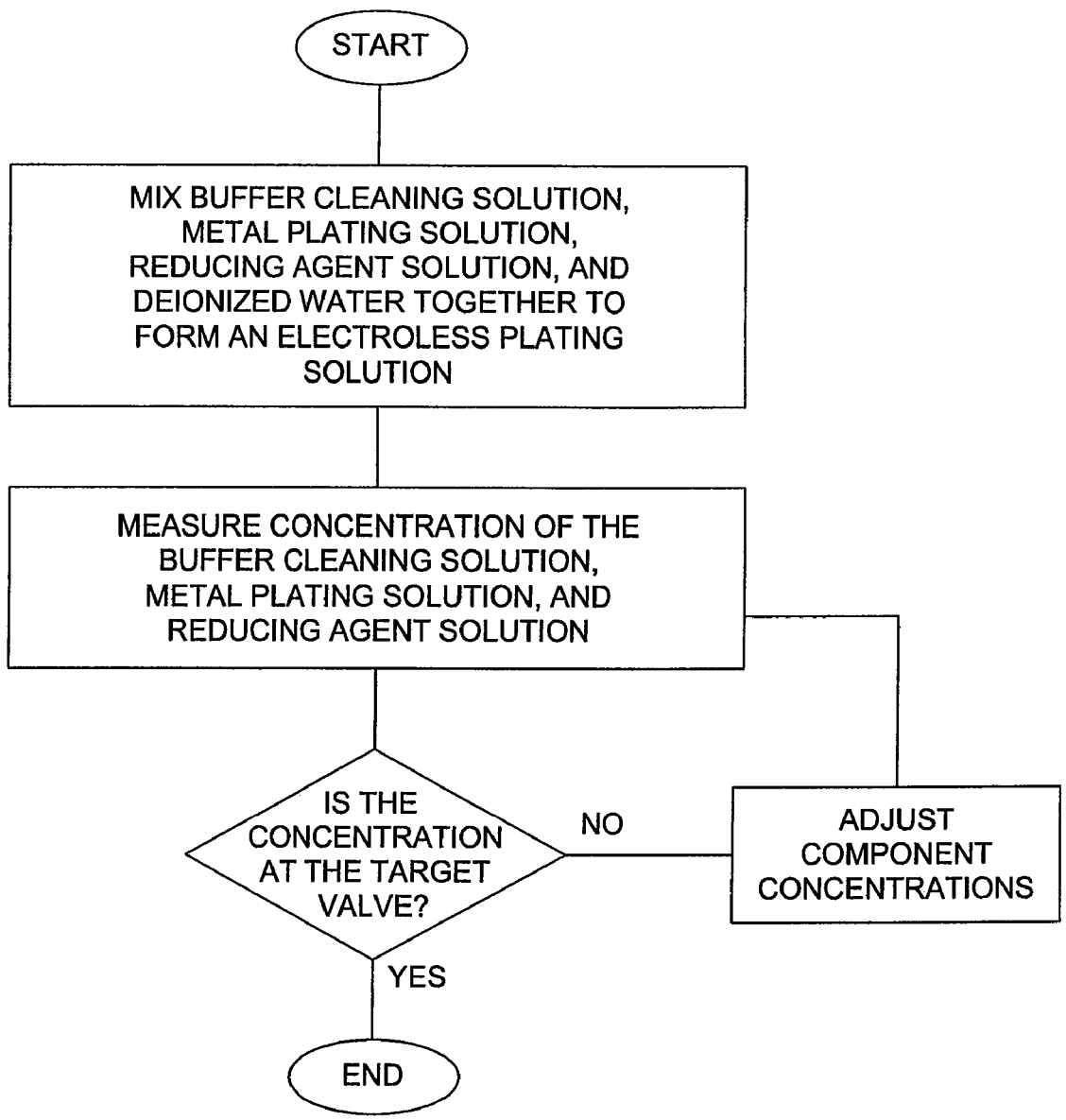
FIG. 3 is a flow chart for measuring the concentration of the individual solutions that make up the electroless plating solution.

FIG. 3 is a flow chart showing one embodiment of the process for measuring the concentration of the individual solutions that comprise the electroless plating solution. After the solutions are mixed together with deionized water, Raman spectroscopy is used to measure the concentration of the electroless plating solution. In one embodiment, deionized water, a buffered solution, a metal solution, and a reducing agent solution are mixed in a 7:1:1:1 ratio. It is difficult for the Raman spectroscopy to measure the components of the buffered solution or the components of the metal solution or the components of the reducing agent solution at this point because the individual components have such a small concentration. It is more challenging for Raman spectroscopy to measure concentrations below 10%. Once the solutions are mixed together, the concentration of the individual components of the solutions is reduced below 10% and hence, is more challenging to measure. Instead, once all of the solutions are mixed together, the concentration of the solutions themselves can be measured. Specifically, the concentration of the buffered cleaning solution can be measured in relation to the entire electroless plating solution. Similarly, the concentration of the metal solution can be measured in relation to the entire electroless plating solution. Finally, the concentration of the reducing agent solution can be measured in relation to the entire electroless plating solution.

It should be understood that while deionized water is discussed as a component of the electroless plating solution, other additives known in the art may be utilized in addition to or in place of deionized water.

Fluid Delivery Hardware

The processes described herein are performed in a processing cell generally configured to expose a substrate to an electroless plating solution, wherein the substrate is in a face-down or a face-up configuration. An electroless fluid plumbing system 402 may be used to provide a continuous series of processing solutions to the processing cell for cleaning and electrolessly depositing a series of layers to form a thin metal film having varying composition on a conductive surface, according to various embodiments of the invention.

It is to be understood that while a three component electroless plating solutions is described below in relation to the fluid delivery hardware, two component electroless plating solutions and electroless plating solutions comprising more than three components are also contemplated. Additionally, while deionized water is discussed as a component of the electroless plating solution, it is to be understood that other additives may be used in addition to or in place of deionized water as is known to those of ordinary skill in the art.

Figure 4:
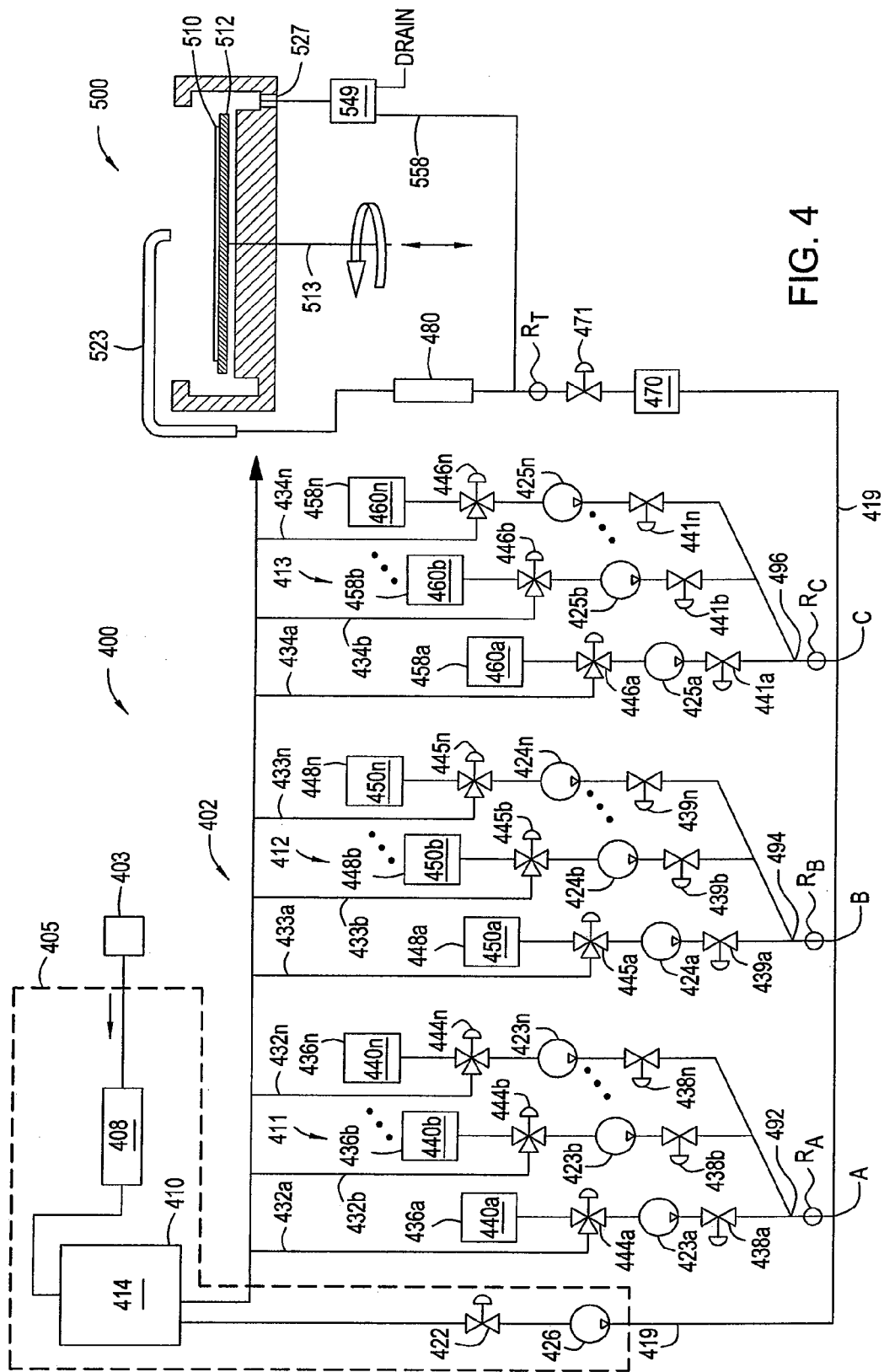
FIG. 4 depicts a perspective and partial sectional view of an exemplary electroless fluid system and electroless plating cell with head assembly for forming a thin metal film, in accordance with various embodiments of the invention.

FIG. 4 generally illustrates a schematic view of an exemplary electroless plating system 400 configured to remove oxides from a conductive surface and subsequently deposit a thin metal layer having a varying composition on the conductive surface in one continuous process. The electroless plating system 400 includes an electroless fluid plumbing system 402 configured to provide a continuous flow of a degassed and preheated DI water, buffered cleaning solution, and a series of electroless processing solutions to a processing cell 500 containing a substrate 510 mounted on a substrate support 512. In one embodiment, as shown in FIG. 4, the processing cell is a face-up type processing cell. In one embodiment, the electroless fluid plumbing system 402 generally contains a DI water source system 405, a buffered cleaning solution system 411, a metal solution delivery system 412, and a reducing agent solution delivery system 413. In general, the DI water source system 405, buffered cleaning solution system 411, metal solution delivery system 412, and reducing agent solution delivery system 413 each contain a container (e.g., items 410, 436*a-n*, 448*a-n*, and 458*a-n*), and a fluid metering device (e.g., items 423*a-n*, 426, 424*a-n*, and 425*a-n*). The container (e.g., items 410, 436*a-n*, 448*a-n*, and 458*a-n*) is generally a vessel that contains an amount of a desired solution that will be mixed with the other components to form one of the processing solutions described above. The fluid metering device (e.g., items 423*a-n*, 426, 424*a-n*, and 425*a-n*) may be a metering pump, liquid flow controller, or needle valve that is used to control the flow rate of a desired component from the container so that it can be mixed with a known flow rate of other components to form a desired electroless processing solution. In some configurations it may be advantageous to use gravity or pressurize one or more of the containers with a gas to help control the flow of the contained fluid. In one aspect, the fluid metering device (e.g., items 423*a-n*, 426, 424*a-n*, and 425*a-n*) is used to dose an amount of a desired component. The timing, flow rate, and dose amount of each of the components is controlled by use of a system controller (not shown) which controls the various components in the electroless fluid plumbing system 402 (e.g., fluid metering devices, isolation valves, etc.). The system controller, which is typically a microprocessor-based controller, is configured to receive inputs from a user and/or various sensors, including the Raman spectroscopy system, in electroless plating system 400 and appropriately control the processing chamber components and electroless fluid plumbing system 402 in accordance with the various inputs and software instructions retained in the controller's memory (not shown). In another aspect of the invention, as shown in FIG. 4, isolation valves (e.g., items 438a-n, 439a-n, and 441a-n) may be added to prevent cross contamination of the fluids retained in the various containers.

In one embodiment, the DI water source system 405 generally contains a water container 410, an in-line degasser 408, a fluid metering device 426 and an isolation valve 422. During operation, a degassed and preheated DI water 414 is prepared by flowing DI water from the DI water source 403 through an in-line degasser 408 to a water container 410 having a heating source. The degassed and preheated DI water 414 serves as both a diluent and a heat source in forming the buffered cleaning solution and/or electroless processing solutions. Passing the DI water through the in-line degasser 408 reduces the amount of dissolved oxygen ($O_2$) normally present in the DI water. The in-line degasser 408 is preferably a contact membrane degasser, although other degassing processes including sonication, heating, bubbling inert gas (e.g., $N_2$ or Ar), adding oxygen scavengers and combinations thereof, may be used. Membrane contactor systems typically involve the use of microporous hollow hydrophobic fibers, generally made from polypropylene, that selectively allow gas diffusion (e.g., $O_2$) while not permitting liquids to pass. The water container 410 may have a heating source (not shown) which heats the DI water 414 to a temperature in the range of about 50 degrees C. to about 95 degrees C. The heating source may also be a microwave heating source external to the water container 410 (a nonmetallic container), an immersed resistive heating element inside the water tank, a resistive heating element surrounding the water tank, a fluid heat-exchanger that is configured to exchange heat with the DI water by use of a heat exchanging body and a temperature controlled fluid flowed therethrough, and/or another method of heating known to heat water. In addition, the degassed and preheated DI water 414 may be hydrogenated prior to use. Saturation of the DI water 414 is preferably saturated with hydrogen gas that may reduce the initiation time of the electroless deposition process. Hydrogenation of the DI water may be completed by bubbling hydrogen gas through the DI water 414, forcing hydrogen gas into DI water 414 while contained in water container 410, and/or by injecting hydrogen into the DI water by use of a contact membrane degasser (not shown).

A flow of a buffered cleaning solution is provided to the processing cell 500 by combining DI water 414 and a buffered cleaning solution concentrate 440a-n stored in containers 436a-n. To form the buffered cleaning solution of a desired concentration, a metered flow of DI water 414 is delivered to insulated line 419 from the water container 410 by use of the fluid metering device 426, and a metered flow of a buffered cleaning solution concentrate 440a-n is injected into the insulated line 419 at point "A", by use of the fluid metering devices 423a-n, to form a flow of buffered cleaning solution at a desired concentration, at a desired temperature, and at a desired flow rate.

Prior to entering the insulated line 419, the buffered cleaning solution concentrate 440a-n has joined together at point 492 to create a buffered cleaning solution. The concentration of the components that comprise the buffered cleaning solution concentration needs to be known. If the components concentration is not at the target value for the desired application, then the buffered solution may not operate effectively and the entire electroplating solution will not function at optimum levels. Raman spectroscopy can be used to measure the concentration of the components that comprise the buffered cleaning solution. A Raman spectrograph, such as described above, can measure the concentration of the components of the buffered cleaning solution at point $R_A$. Point $R_A$ may be a metrology window or a sample of the solution as discussed above. If the concentration of the components is not at the target value, the concentration of the components can be adjusted. The buffered cleaning solution that has the incorrect concentration may be discarded or recycled as discussed above. The concentration can be adjusted by altering the flow rate of the individual components through the isolation valves 438a-n and the deionized water through the three way valves 444a-n.

To form a first processing solution, containing a buffered cleaning solution and a first metal solution a metered flow of a first metal solution is added to the flowing buffered cleaning solution in the insulated line 419 at about point "B". The first metal solution 450a stored in container 448a is metered into the insulated line 419 at about point "B", by use of a fluid metering device 424a, where the first metal solution is fed into the flow of buffered cleaning solution concentrate 440 and DI water 414 to form a the buffered cleaning solution and a first metal solution described as described in step 104 that has a desired concentration of the various components, at a desired temperature, and at a desired flow rate. The combined flow of buffered cleaning solution and first metal solution has a flow rate in the range of about 100 ml/min to about 800 mL/min and is delivered to the processing cell 500 for a period of about 5 seconds to about 30 seconds to remove the oxides from the conductive surface. In one aspect, the concentration and types of buffered cleaning solutions and first metal solutions can be varied as desired by varying the flow rate of the various metal solutions 450a through 450n, DI water 414, and buffered cleaning solutions concentrate 440.

Prior to entering the insulated line 419, the metal solution concentrate 450a-n has joined together at point 494 to create a metal solution. The concentration of the components that comprise the metal solution concentration needs to be known. If the components concentration is not at the target value for the desired application, then the metal solution may not operate effectively and thus, the entire electroplating solution will not function at optimum levels. Raman spectroscopy can be used to measure the concentration of the components that comprise the metal solution. A Raman spectrograph, such as described above, can measure the concentration of the components of the metal solution at point $R_B$. Point $R_B$ may be a metrology window or a sample of the solution as discussed above. If the concentration of the components is not at the target value, the concentration of the components can be adjusted. The metal solution that has the incorrect concentration may be discarded or recycled as discussed above. The concentration can be adjusted by altering the flow rate of the individual components through the isolation valves 439a-n and the deionized water through the three way valves 445a-n.

To form an electroless plating solution, a flow of a first reducing agent solution is added to the combined flow of buffered cleaning solution and first metal solution in insulated line 419 at about point "C" to deliver a first electroless bath solution to the processing cell 500. In one embodiment, as the flow of the first reducing agent solution is introduced and the total (or combined) flow rate is increased, the flow DI water is decreased so that the total flow rate and temperature will remain constant. The first reducing agent solution is delivered at a desired flow rate to the insulated line 419 at about point "C" by use of the fluid metering device (e.g., one or more of the items 425a-n) thereby forming a flow of a first electroless plating solution. The flow of the first electroless plating solution comprising the buffered cleaning solution, the first metal solution, the first reducing agent solution and DI water 414, typically has a flow rate in the range of about 100 ml/min to about 1000 mL/min and is delivered to the processing cell 500 for a period of about 5 seconds to about 60 seconds to plate a fist metal layer on the conductive surface of the substrate 510. The flow of the first electroless plating solution is preferably delivered to the processing cell 500 via an in-line mixer 470 and an in-line heater 480. In-line heating may be accomplished by jacketing the fluid lines with a flowing heat exchanging fluid or by using an in-line microwave heater such as a microwave cavity.

Prior to entering the insulated line 419, the reducing agent solution concentrate 460a-n has joined together at point 496 to create a reducing agent solution. The concentration of the components that comprise the reducing agent solution concentration needs to be known. If the components concentration is not at the target value for the desired application, then the reducing agent solution may not operate effectively and thus, the entire electroplating solution will not function at optimum levels. Raman spectroscopy can be used to measure the concentration of the components that comprise the reducing agent solution. A Raman spectrograph, such as described above, can measure the concentration of the components of the reducing agent solution at point $R_C$. Point $R_C$ may be a metrology window or a sample of the solution as discussed above. If the concentration of the components is not at the target value, the concentration of the components can be adjusted. The reducing agent solution that has the incorrect concentration may be discarded or recycled as discussed above. The concentration can be adjusted by altering the flow rate of the individual components through the isolation valves 441a-n and the deionized water through the three way valves 446a-n.

Once all of the solutions that comprise the electroless plating solution are mixed together, the concentration of the solutions themselves can be measured. It is important to note that the concentration of the components that comprise the individual solutions is difficult to measure once the solutions are mixed together because the concentration of the individual components is below the level that they can reasonably be detected by Raman spectroscopy. The concentration of the individual components that comprise the individual solutions is low because, once combined with the other solutions and their components and the deionized water, the concentration of the individual components decreases to below 10%. Of course, if no deionized water were used, then any component with a concentration level above 10% could be easily measured with Raman spectroscopy.

Raman spectroscopy can be used to measure the concentration of the solutions that comprise the electroless plating solution. A Raman spectrograph, such as described above, can measure the concentration of the components of the reducing agent solution at point $R_T$. Point $R_T$ may be a metrology window or a sample of the solution as discussed above. The electroless plating solution that has the incorrect concentration may be discarded or recycled as discussed above. If the concentration of any one solution is not at the target value for the desired application, the concentration for the solutions can be adjusted accordingly by adjusting the flow rates of the solutions and the deionized water through the isolation valves (i.e., 422, 438a-n, 439a-n, and 441a-n).

In one aspect, subsequent metal layers can be formed by varying the flow rate of metal solutions 450a through 450n, reducing agent solutions 460a through 460n, DI water 414, and buffered cleaning solutions concentrate 440a-n to provide a series of electroless plating solutions to the processing cell 500 for depositing a series of metal layers over the conductive surface 6A.

In one embodiment, to assure that the concentration of the various components flowing in the insulated line 419 to the substrate 510 will not vary as one or more chemical components are phased out of the flowing fluid, for example where it is desired to change the composition of the electrolessly deposited layer, it may be necessary to add a fluid into the flowing fluid in proportion to the flow of the phased out component(s). For example, if it is desirable to phase "out" a 50 mL/min flow of the first metal solution 450a, then a 50 mL/min flow of DI water is phased "in" to assure that the total flow in the insulated line 419 does not change and the proportions of the components already flowing in the line are not changed. Referring to FIG. 4, this process may be accomplished by use of the three-way valves (e.g., items 444a-n, 445a-n, and 446a-n) connected DI water lines (e.g., items 432a-n, 433a-n, and 434a-n) and the fluid metering device (e.g., items 423a-n, 424a-n, and 425a-n). When in use the three-way valve is used to switch between a container and its associated DI water line, so that the fluid metering device is able to deliver a flow of DI water at the same rate as the previous flow of the fluid delivered from the container.

In one aspect, the three-way valves (e.g., items 444a-n, 445a-n, and 446a-n) connected DI water lines (e.g., items 432a-n, 433a-n, and 434a-n) and the fluid metering device (e.g., items 423a-n, 424a-n, and 425a-n) may be used together to provide an intermediate dilution or rinsing step before the introduction of a new component solution into the insulated line 419.

Substrate to Substrate Process Control

In another aspect, the concentration of the electroless plating solution(s) used to perform the electroless deposition process are varied from one substrate to another substrate to account for changes in the density, surface area, or shape of the conductive surfaces found on the substrate surface. The process can be adjusted based on user input or automated inspection data collected regarding the conductive surface characteristics. Automated inspection tools may include pattern wafer optical wafer inspection tools, Boxer Cross, and SEM-EDX techniques that are adapted to collect information regarding the surface of the substrate.

Based on the collected data the system controller is adapted to adjust the various processing chemistries by commands from one or more process recipes contained in the memory of the system controller. The concentrations of the various processing chemistries may be varied by controlling the flow rate of metal solutions 450a through 450n, reducing agent solutions 460a through 460n, DI water 414, and buffered cleaning solution concentrates 440a-n to provide a series of cleaning and electroless plating solutions to the processing cell 500 for depositing a layer having desired properties over the conductive surface. For example, in order to maximize the efficiency of cobalt utilization (and minimize amount of cobalt in waste streams) the concentration of cobalt in the processing chemistries may be reduced when the ratio of the copper surface area to the dielectric surface area is smaller than another case where the ratio of the copper surface area to the dielectric surface area is higher.

Ratios of individual components and/or levels of a specific additive such as a stabilizer may also be varied during the growth of an electroless coating either to enhance or eliminate an observed dependence of growth rate on pattern size and density. Raman spectroscopy may be used to ensure that the concentration is adjusted correctly. For example, while it is generally desirable to initiate film growth using a formulation established to promote rapid initiation and growth on all exposed surfaces, once the process has initiated the concentration of critical components may be adjusted by changing the relative mixing ratios of component solutions to enhance or inhibit deposition on small isolated features relative to larger features. An isolated feature is a feature that is in a region on the surface of the substrate where density of the conductive surfaces is low (e.g., low ratio of copper surface area to the dielectric surface area). Plating formulations exhibiting diffusion limited plating rates, which may be tied to the concentration of a single dilute component (e.g., the concentration of a metal ions), will generally exhibit substantially faster growth over isolated features when plated using a static puddle mode than when experiencing dynamic flow. However, low concentrations of certain stabilizers or additional metal precursors can be used to compensate for or actually reverse such effects by exhibiting greater inhibitory effects on small isolated features relative to larger features. This effect may be particularly obvious when using a static "puddle" plating mode (e.g., small to no fluid motion relative to the surface of the substrate). The ability to adjust the individual processing chemistries to a specific substrate pattern is thus an advantage. By using Raman spectroscopy as taught above, the specific components of the solution may be measured to ensure a specific processing chemistry.

Therefore, it may be desirable to vary the metal ion concentration, stabilizer concentration, and other electroless plating components based on the surface properties of the substrate and/or during different phases of the process to compensate for the deposition rate variation on the small isolated features and the larger features. For example, it may be advantageous to use an electroless plating chemistry that does not contain a stabilizer during the first initiation phases of the electroless deposition process to assure that the electroless deposition process initiates at the same time on all features and then change the composition of the electroless plating solution by adding a solution that contains a stabilizer to compensate for the deposition rate difference on the small isolated features and large features.

Recirculation Hardware

In one embodiment, the processing is performed by forming an electroless plating solution using the process(es) described above and then delivered to the surface of the substrate 510. The flow of the electroless plating solution is continued until the electroless plating solution covers the substrate 510, flows over the edge of the substrate 510, and then fills a collection tank system 549. The collection tank system 549 generally contains a vessel (not shown) and a recirculation pump (not shown) that are adapted to recirculate the collected electroless plating solution collected in the collection tank system 549. After a desirable amount of the electroless plating solution is retained in the collection tank system 549 the isolation valve 471 is closed and the recirculation pump is used to cause a continuous flow of the collected fluid to the substrate 510 surface. The recirculation pump causes the collected fluid to flow through the insulated line 558, through the in-line heater 480 and out the nozzle 523 where it is dispensed on the substrate 510 and then recollected in the vessel contained in the collection tank system 549 so that it can be recirculated again by the recirculation pump. The flow rate of the collected electroless plating solution may range of about 100 ml/min to about 1000 mL/min.

Chamber Face-up Hardware

Figure 5:
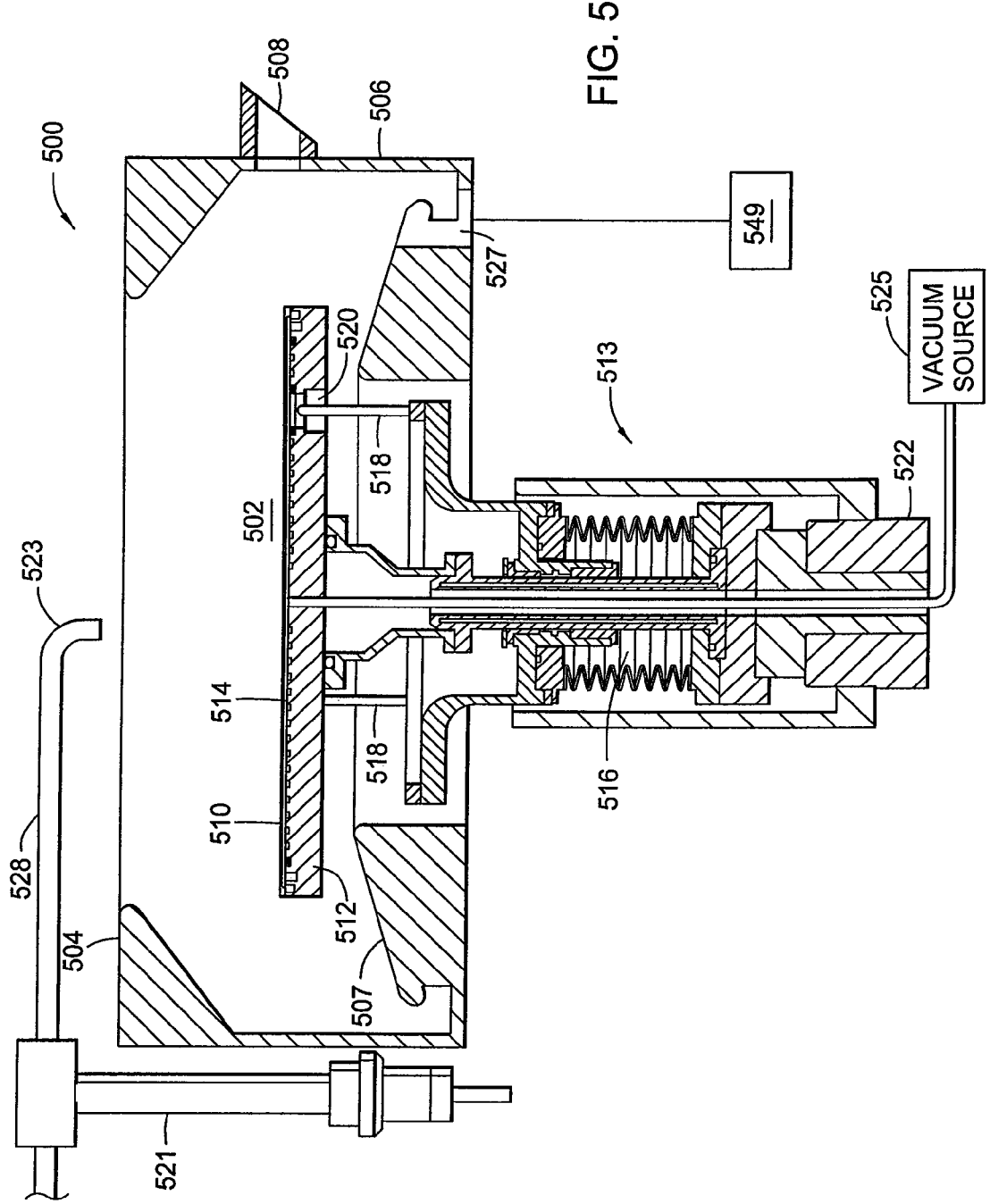
FIG. 5 schematically depicts a partial cross-sectional view of an exemplary face up type electroless fluid processing cell, in accordance with an embodiment of the invention.

FIG. 5 shows a schematic cross-sectional view of one embodiment of a processing cell 500 useful for the deposition of an electroless layer as described herein. The processing cell 500 includes a processing compartment 502 comprising a top 504, sidewalls 506, and a bottom 507. A substrate support 512 is disposed in a generally central location in the processing cell 500 has a vacuum source 525 for vacuum chucking the substrate 510 to the substrate support 512. The substrate support 512 includes a substrate receiving surface 514 to receive the substrate 510 in a "face-up" position. In one aspect, having the substrate 510 disposed on the substrate support 512 in a "face-up" position reduces the possibility of bubbles in a fluid when applied to the substrate 510 from affecting the processing of the substrate 510. For example, bubbles may be created in the fluid in-situ, created in the fluid handling equipment, or may be created by transferring of a wet substrate. If the substrate was disposed in a "face-down position" during processing, bubbles in the fluid would be trapped against the surface of the substrate as a result of the buoyancy of the bubbles. Having the substrate in a "face-up" position reduces bubbles in the fluid from being situated against the surface of the substrate since the buoyant forces causes the bubbles to rise up in the fluid. Having the substrate in a face-up position also lessens the complexity of the substrate transfer mechanisms, improves the ability to clean the substrate during processing, and allows the substrate to be transferred in a wet state to minimize contamination and/or oxidation of the substrate.

The substrate support 512 may comprise a ceramic material (such as alumina $Al_2O_3$ or silicon carbide (SiC)), TEFLON™ coated metal (such as aluminum or stainless steal), or other suitable polymer materials. TEFLON™ as used herein is a generic name for fluorinated polymers such as Tefzel (ETFE), Halar (ECTFE), PFA, PTFE, FEP, PVDF, etc. Preferably, the substrate support 512 comprises alumina. The substrate support 512 may further comprise embedded heated elements, especially for a substrate support comprising a ceramic material or a polymer material.

The processing cell 500 further includes a slot 508 or opening formed through a wall thereof to provide access for a robot (not shown) to deliver and retrieve the substrate 510 to and from the processing cell 500. Alternatively, the substrate support 512 may raise the substrate 510 through the top 504 of the processing compartment to provide access to and from the processing cell 500.

A lift assembly 516 may be disposed below the substrate support 512 and coupled to lift pins 518 to raise and lower lift pins 518 through apertures 520 in the substrate support 512. The lift pins 518 raise and lower the substrate 510 to and from the substrate receiving surface 514 of the substrate support 512.

A motor 522 may be coupled to the substrate support 512 to rotate the substrate support 512 to spin the substrate 510. In one embodiment, the lift pins 518 may be disposed in a lower position below the substrate support 512 to allow the substrate support 512 to rotate independently of the lift pins 518. In another embodiment, the lift pins 518 may rotate with the substrate support 512.

The substrate support 512 may be heated to heat the substrate 510 to a desired temperature. The substrate receiving surface 514 of the substrate support 512 may be sized to substantially receive the backside of the substrate 510 to provide uniform heating of the substrate 510. Uniform heating of a substrate is an important factor in order to produce consistent processing of substrates, especially for deposition processes having deposition rates that are a function of temperature. In one embodiment, it may be desirable to deliver the fluid processing solution(s), described above, at a temperature lower than the temperature of the substrate support (e.g., the electroless processing temperature) to reduce the chance of particle formation in the fluid processing solution prior to being dispensed on the substrate surface.

A fluid input, such as a nozzle 523, may be disposed in the processing cell 500 to sequentially deliver the buffered cleaning solution and a series of electroless plating solutions, and deionized water, to the surface of the substrate 510. The nozzle 523 may be disposed over the center of the substrate 510 to deliver a fluid to the center of the substrate 510 or may be disposed in any position. The nozzle 523 may be disposed on a dispense arm 528 positioned over the top 504 or through the sidewall 506 of the processing compartment 502. The dispense arm 528 may be moveable about a rotatable support member 521 which is adapted to pivot and swivel the dispense arm 528 and the nozzle 523 to and from the center of the substrate 510. Additionally or alternatively, a nozzle (not shown) may be disposed on the top 504 or sidewalls 506 of the processing cell 500 and adapted to spray a fluid in any desired pattern on the substrate 510.

The processing cell 500 further includes a drain 527 in order to collect and expel fluids used in the processing cell 500. The bottom 507 of the processing compartment 502 may comprise a sloped surface to aid the flow of fluids used in the processing cell 500 towards an annular channel in communication with the drain 527 and to protect the substrate support assembly 513 from contact with fluids.

A more detailed description of face-up processing cell may be found in the commonly assigned U.S. Patent Application Publication Number 2003/0141018 A1, entitled "Electroless Deposition Apparatus" by Stevens et al., published Jul. 31, 2003, which is incorporated by reference herein in its entirety.

Chamber Face-Down Hardware

Figure 6:
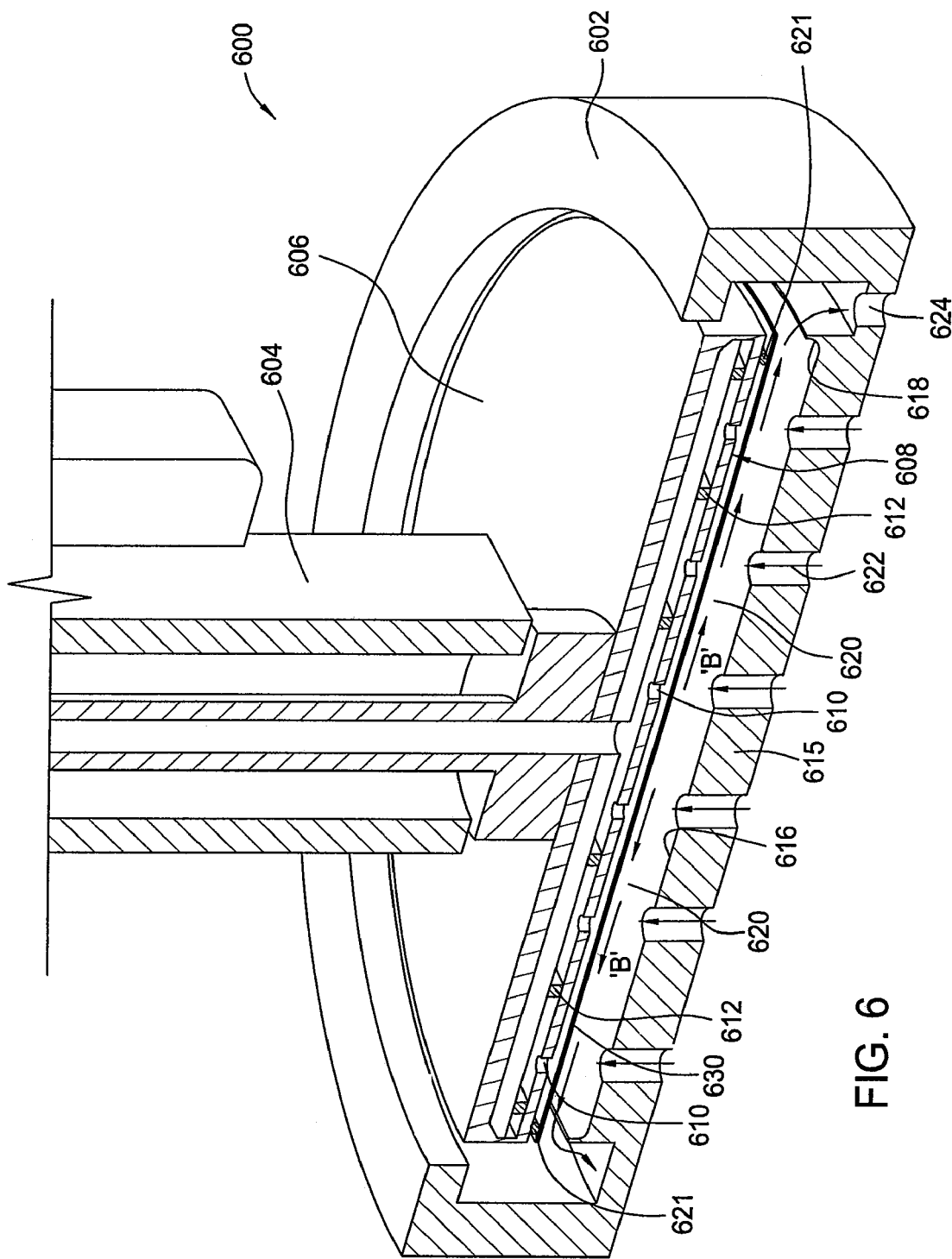
FIG. 6 schematically depicts a partial cross-sectional view of an exemplary face down type electroless fluid processing cell, in accordance with an embodiment of the invention.

As illustrated in FIG. 6, the fluid processing cell 600 may be a face-down type fluid processing cell including a head assembly 604 configured to support a substrate 630 oriented such that the production surface is face down and to move the substrate downwards into a processing fluid provided in a cell body 602. The head assembly 604 generally includes a substrate support member 606 that is configured to rotate, horizontally or pivotally actuate, and vertically actuate as well as being sized to be received within the opening of cell body 602. The substrate support member 606 includes a substantially planar lower surface 608 that has a plurality of vacuum apertures 610 formed therein. The lower surface may be coated or manufactured from a material that is nonreactive with fluid processing solutions, such as ceramics or plastics. The vacuum apertures 610 are selectively in fluid communication with a vacuum source (not shown) such that the vacuum apertures 610 may be used to vacuum chuck a substrate 630 to the lower surface 608. An annular seal 621, such as an o-ring type seal, for example, near the perimeter of the substrate support surface 608 is configured to engage the backside of the substrate 630 to create a vacuum tight seal between the lower surface 608 and the substrate 630 while also preventing fluids from contacting the backside of the substrate. The interior of the substrate support member 606 may include a heater assembly 612, which may comprise a plurality of concentrically positioned heating bands. The heating bands may include resistive heaters, fluid passages configured to have a heated fluid flowed therethrough, or another method of heating a substrate support member for a semiconductor processing method. The plurality of heating bands may be individually controlled, if desired, to more accurately control the substrate temperature during processing. More particularly, individual control over the heating bands allows for precise control over the deposition temperature, which is critical to electroless plating processes. The substrate support member 606 may further include an actuator or vibration device (not shown) configured to impart megasonic or other vibrational energy to substrate 614 during processing.

The cell body 602 may be manufactured from various substances known to be nonreactive with fluid processing (i.e., electroless or ECP) solutions, such as plastics, polymers, and ceramics, for example. A bottom central portion of the cell body 602 includes a fluid processing basin 615. The basin 615 generally includes a substantially planar basin surface 616 having an annular fluid weir 618 circumscribing the basin surface 616. The fluid weir 618 generally has a height of between about 2 mm and about 20 mm, and is generally configured to maintain a processing fluid in a puddle-type configuration on the basin surface 616 in a processing region 620. The basin surface 616 also includes a plurality of fluid apertures 622 formed therein. The fluid apertures 622 are generally in fluid communication with a plurality of processing fluid sources, such as rinsing solution sources, activation solution sources, cleaning solution sources, electroless plating solution sources, and other fluid sources that may be used in an electroless deposition process. As such, apertures 622 may be used to supply processing fluids to the processing region 620. The processing fluid will generally flow upward through the apertures 622, and then outward through the processing region 620 toward weir 618, as indicated by arrows "B". A fluid drain 624 is generally positioned in an outer lower portion of the cell body 602, generally outward of the fluid weir 618. As such, the fluid drain 624 is configured to collect fluid that overflows weir 618. The face down-type electroless plating cells, and processing platforms, described herein are more fully described in the commonly assigned U.S. Pat. No. 6,824,612, which is incorporated by reference herein in its entirety.

Fluid Delivery Process

In one aspect of the process, the various fluid processing solutions are delivered to the surface of a substrate using a continuous flow of fluid. The term fluid processing solutions is generally meant to describe various processing fluids, electroless plating solutions and/or rinse solutions. In this configuration the total flow of the fluid processing solutions used to perform the various processing steps may be varied as desired to meet the processing needs, but the flow of the fluid processing solutions onto the substrate surface is usually greater than zero. The use of an uninterrupted flow may be advantageous to assure that a fresh concentration of solution is continually delivered to the substrate surface to minimize process variations caused by changing chemical concentrations during processing and reduce the chance of surface oxidation. Also, the use of an uninterrupted flow will minimize the total chamber processing time, since time is not wasted completing non-value added steps, such as, adding and removing the chemical from the surface of the substrate.

In another aspect, the flow of the fluid processing solutions are paused for a user defined period of time once the delivered fluid processing solution covers the substrate surface. The flow is then reinitiated after the user defined time has expired so that the next fluid processing solution can be delivered to the substrate surface. This configuration thus allows the fluid processing solution retained on the surface of the substrate, time to complete the desired process, while reducing the process chamber waste. This configuration may also prevent or minimize the exposure of the surface of the substrate to possible sources of oxygen or other contaminants, by assuring that the substrate surface is covered with a fluid processing solution.

In another aspect, a flow of a first fluid processing solution is dispensed and retained on the surface of a substrate for a period of time and then a second fluid processing solution is added to the volume of the first fluid processing solution and retained on the surface of the substrate for a second user defined period of time. In one aspect it may be advantageous to use a first fluid processing solution and a second fluid processing solution that have a different composition so that two layers having a different composition can be deposited in one continuous process. In one aspect, it may also be advantageous to dispense a first volume of the first processing fluid that has a smaller volume than the volume of the second fluid so that the first processing solution doesn't significantly dilute the solution formed when the second solution is added to the first solution. In one aspect, it may also be advantageous to dispense the first processing solution, and other processing fluids, using a spray or mist dispense process to get fast and uniform coverage of the surface substrate surface. This configuration thus allows the thin layer of fluid retained on the surface of the substrate, time to complete their respective processes, while reducing the process chamber waste. This configuration may also prevent or minimize the exposure of the surface of the substrate to possible sources of oxygen or other contaminants, by assuring that the substrate surface is covered with a fluid processing solution.

In yet another aspect, it may be advantageous to remove the fluid processing solution covering the substrate surface by, for example, rotating the substrate, after one step is completed but before the flow of the next fluid processing solution is reinitiated to reduce the dilution effect caused by mixing the two fluid processing solutions. In this case the exposure of the substrate surface to the atmosphere may be minimized to reduce the chance of oxidation or contamination by assuring the fluid processing solution removal process leaves the substrate surface "wet" with the original fluid processing solution. This step may be completed by reinitiating the flow of the next fluid processing solution before the substrate surface is completely removed. In one aspect, the use of fluid processing solutions that contain DEA, TEA, surfactants and/or other wetting agents can reduce the likelihood of exposure of the conductive surfaces since the use of this component will reduce the likelihood of evaporation and/or drying of the surfaces exposed to the fluid processing solution. In one aspect, the flow of the next fluid processing solution is initiated at the same time the process of removing the prior fluid processing solution begins to minimize the exposure of the substrate surface to oxygen or other contaminants.

It is to be understood that the solutions that are measured need not be mixed to create the solution, but rather, may be a solution that is purchased from a supplier as a stock solution at the desired concentration. In such a scenario, the chemical concentration of the stock solution may be verified by Raman spectroscopy as well. For example, a stock solution may be added to a processing system and then the chemical concentration of the stock solution may be verified to allow a technician to determine whether or not to provide the solution to the desired process. In another embodiment, stock solutions may be mixed together to form a solution that may also be measured by Raman spectroscopy as discussed above.

Knowing the concentration of the solutions that comprise an electroless plating solution is beneficial because it allows a technician the ability to adjust the concentration whenever it does not meet the target value. Similarly, adjusting the composition of the electroless plating solution as a whole is beneficial to ensure that the target valve for the concentration of the electroplating solution is met. Raman spectroscopy provides an effective means to achieve both results.

While the foregoing is directed to embodiments of the present invention, other and further embodiments of the invention may be devised without departing from the basic scope thereof, and the scope thereof is determined by the claims that follow.

The invention claimed is:

1. An electroless deposition method, comprising:
   monitoring a concentration of chemicals in an electroless solution using Raman spectroscopy;
   comparing results from the Raman spectroscopy with a stored value;
   adjusting the concentration of a chemical in the solution or discarding the solution based on the comparing results from the Raman spectroscopy with the stored value; and
   providing the electroless solution to an electroless plating cell, wherein a substrate is provided in a face-up position within the electroless plating cell.

2. An electroless deposition method comprising:
   monitoring a concentration of chemicals in an electroless solution using Raman spectroscopy;
   comparing results from the Raman spectroscopy with a stored value;
   adjusting the concentration of a chemical in the solution or discarding the solution based on the comparing results from the Raman spectroscopy with the stored value; and
   providing the electroless solution to an electroless plating cell, wherein a substrate is provided in a face-down position within the electroless plating cell.

3. The method of claim 2, wherein the electroless solution comprises a reducing agent and a metal.

4. An electroless deposition method comprising:
   combining a buffered cleaning solution with a metal solution and a reducing agent solution to form an electroless solution;
   monitoring a concentration of chemicals in the electroless solution using Raman spectroscopy;
   comparing results from the Raman spectroscopy with a stored value; and
   adjusting a concentration of the buffered cleaning solution, the metal solution, and the reducing agent solution within the electroless solution based upon comparing results from the Raman spectroscopy.

5. The method of claim 4, wherein the buffered solution, the metal solution and reducing agent solution each comprise a plurality of individual components, further comprising:
   monitoring the individual components of each of the buffered solution, the metal solution and the reducing agent solution using Raman spectroscopy, wherein the monitoring occurs prior to combining the buffered solution, the metal solution, and the reducing agent solution.

6. The method of claim 5, further comprising:
   adjusting the individual components of the buffered solution, the metal solution, and the reducing agent solution based upon the monitoring of the individual components.

7. An electroless deposition method, comprising:
   measuring a concentration of components of a metal solution using Raman spectroscopy;
   measuring a concentration of components of a reducing agent solution using Raman spectroscopy;
   combining the metal solution and the reducing agent solution to form a electroless solution; and
   dispensing the solution on a surface of a substrate.

8. The method of claim 7, further comprising providing the electroless solution to an electroless plating cell, wherein the substrate is provided in a face-up position within the electroless plating cell.

9. The method of claim 7, further comprising providing the electroless solution to an electroless plating cell, wherein the substrate is provided in a face-down position within the electroless plating cell.

10. The method of claim 7, further comprising adjusting a composition of the metal solution based upon the results of the Raman spectroscopy.

11. The method of claim 7, further comprising adjusting a composition of the reducing agent solution based upon the results of the Raman spectroscopy.

12. The method of claim 7, further comprising:
measuring a concentration of the metal solution and the reducing agent solution in the electroless solution using Raman spectroscopy prior to plating the substrate.

13. The method of claim 12, further comprising adjusting a concentration of the metal solution within the electroless solution based upon the results of the Raman spectroscopy.

14. The method of claim 12, further comprising adjusting a concentration of the reducing agent solution within the electroless solution based upon the results of the Raman spectroscopy.

15. The method of claim 12, further comprising providing the electroless solution to an electroless plating cell, wherein the substrate is provided in a face-up position within the electroless plating cell.

16. The method of claim 12, further comprising providing the electroless solution to an electroless plating cell, wherein the substrate is provided in a face-down position within the electroless plating cell.

17. An electroless apparatus, comprising:
a fluid delivery system; and
a Raman spectrometer positioned to measure a concentration of a fluid without drawing a sample from the system wherein:
the fluid is an electroless solution formed by mixing stock solutions together and wherein the spectrometer is positioned to measure the concentration of the fluid prior to mixing the stock solutions together.

18. An apparatus, comprising:
an electroless plating solution system having a plurality of electroless plating solution component solution sources;
at least one Raman spectrometer coupled with the apparatus, the spectrometer coupled at a location to measure a composition of each component solution source prior to mixing with additional solution component solutions;
at least one metrology window coupled with the Raman spectrometer.

* * * * *